United States Patent [19]

Larsson

[11] Patent Number: 5,201,088
[45] Date of Patent: Apr. 13, 1993

[54] PATIENT EXAMINATION TABLE HAVING A SIMPLIFIED TILT MECHANISM

[75] Inventor: Sten Larsson, Vaellingby, Sweden

[73] Assignee: Siemens Aktiengesellschaft, Munich, Fed. Rep. of Germany

[21] Appl. No.: 802,222

[22] Filed: Dec. 4, 1991

[30] Foreign Application Priority Data

Dec. 12, 1990 [SE] Sweden ............................... 90039686

[51] Int. Cl.⁵ .............................................. A61G 7/00
[52] U.S. Cl. .......................................... 5/610; 5/601; 74/606 R; 74/384; 474/150
[58] Field of Search ........................... 5/601, 610, 611; 378/208, 209; 74/606 R, 384, 380, 421, 98; 474/148, 150

[56] References Cited

U.S. PATENT DOCUMENTS

| | | | |
|---|---|---|---|
| 1,270,737 | 6/1918 | Hyatt | 5/610 |
| 2,347,900 | 5/1944 | Frazer | 74/98 |
| 2,830,479 | 4/1958 | Finn | 74/384 |
| 3,069,543 | 12/1962 | Sazavsky | 5/601 |
| 3,525,308 | 8/1970 | Koopmans . | |
| 4,156,815 | 5/1979 | Hogan | 5/601 |
| 4,842,259 | 6/1989 | Rice | 5/601 |
| 4,894,855 | 1/1990 | Kresse . | |
| 4,912,754 | 3/1990 | Van Steenburg | 378/209 |
| 5,013,018 | 5/1991 | Sicek | 5/601 |

OTHER PUBLICATIONS

Siemens-Elema Brochure for KOORDINAT 3 D II Angiography Examination Table with Ceiling Suspension.

Siemens-Elema Brochure for CIRRUS Ceiling Suspended, Tiltable Table.

Primary Examiner—Michael F. Trettel
Assistant Examiner—F. Saether
Attorney, Agent, or Firm—Hill, Steadman & Simpson

[57] ABSTRACT

A patient examination table, of the type used in an x-ray examination apparatus, has one end secured to a ceiling or floor stand via a tilt mechanism which permits the longitudinal axis of the table to be tilted upwardly or downwardly. The table can be tilted around an imaginary axis, the imaginary axis being movable roughly in the middle of the examination table. The tilt mechanism includes a driven element, which may be a part of the housing for the tilt mechanism, a first gear which is rigidly attached to the stand, a second gear which is rigidly attached to the examination table and a transmission linkage between the first and second gears which permits the second gear to be movable around the drive shaft of the first gear as the driven element is rotated. The second gear is rotated in an opposite direction to the direction of rotation of the driven element.

11 Claims, 3 Drawing Sheets

PATIENT EXAMINATION TABLE HAVING A SIMPLIFIED TILT MECHANISM

BACKGROUND OF THE INVENTION

1. Field of the Invention

The present invention is directed to a patient examination table of the type used to conduct an x-ray examination, the table having one end secured to a ceiling or a floor stand via a mechanism which permits the longitudinal axis of the examination table to be tilted upwardly or downwardly.

2. Description of the Prior Art

A commercially available examination table for a patient in an x-ray apparatus is described in the "KOORDINAT 3D II" brochure (Siemens). This examination table is tiltable at one end, which is secured to a ceiling stand which also permits the examination table to be laterally displaced. The examination table is tiltable so that the longitudinal axis thereof can be moved upwardly or downwardly, and the stand can be extended so that the table is also adjustable in height. In this known apparatus, tilting of the examination table is undertaken manually. For example, if an x-ray examination is to be undertaken in the region of the stomach of the patient, the stand for the x-ray tube and for the image intensifier, as well as the examination table, must be re-positioned in order to enable tilting of the examination table around the stomach of the patient, because the table would otherwise collide either with the x-ray tube or with the image intensifier.

Another commercially available x-ray examination table is disclosed in the "CIRRUS" brochure (Siemens). This examination table is also secured to a ceiling stand, which enables longitudinal, lateral and height displacement of the table. The examination table is also rotatable around a shaft arranged directly beneath the table, and displaced with respect to the middle of the table. The examination table is also provided with an electrical control system having a follower controller by means of which the table can be controlled so that the region to be examined is always located in an isocenter. In the course of an x-ray examination of the chest or the stomach of the patient, the examination table can be tilted around this region by means of the follower controller, without the risk that the patient or the table will collide with the x-ray tube or with the image intensifier.

SUMMARY OF THE INVENTION

It is an object of the present invention to provide an examination table of the type having one end secured to a ceiling or floor stand, and which has a longitudinal axis which is tiltable upwardly or downwardly, wherein the examination table can be tilted around an imaginary axis which can be moved in space roughly in the middle of the examination table.

It is a further object of the present invention to provide such an examination table wherein the tilting is accomplished using a relatively simple, and therefore, inexpensive mechanism.

The above object is achieved in an examination table constructed in accordance with the principles of the present invention wherein a tilt mechanism is provided having a first gear which is rigidly attached to the stand, a second gear which is rigidly attached to the examination table, for a driveable element rotating the second gear around the shaft of the first gear, and a transmission means linking the first and second gears so that the second gear is rotated in a direction opposite to the direction of rotation of the driveable element. A tilt mechanism is achieved which is very simple in structure, and which permits the examination table to be tilted generally around its central region. Because the tilt mechanism is secured at one end face of the examination table, no mechanical parts are present in the tilting region of the table, so that good accessibility for the attending personnel and for the x-ray equipment is established.

In one embodiment of the invention, the tilt mechanism contains an uneven number (at least three) of gears, which mesh with each other in sequence. This tilt mechanism structure is extremely stable.

In a further embodiment of the invention, at least one arm is provided, which proceeds parallel to the gears, and to which the respective shafts of the gears are attached.

In a further modification of this embodiment, a further arm may be attached to the opposite side of the gears. One of the arms may form a housing for the tilt mechanism, and the other arm may form a cover for the housing. The number of parts for the tilt mechanism is thus reduced.

In another modification of this embodiment, one of the arms forms the driveable element and is connected to a drive means for rotating the arm around the shaft of the first gear. The drive means preferably includes a drive wheel having a shaft which also forms the shaft for the first gear. The drive wheel is connected to a drive motor. A simple control of the tilting of the examination table is thereby achieved.

DESCRIPTION OF THE PREFERRED EMBODIMENTS

Figure 1:
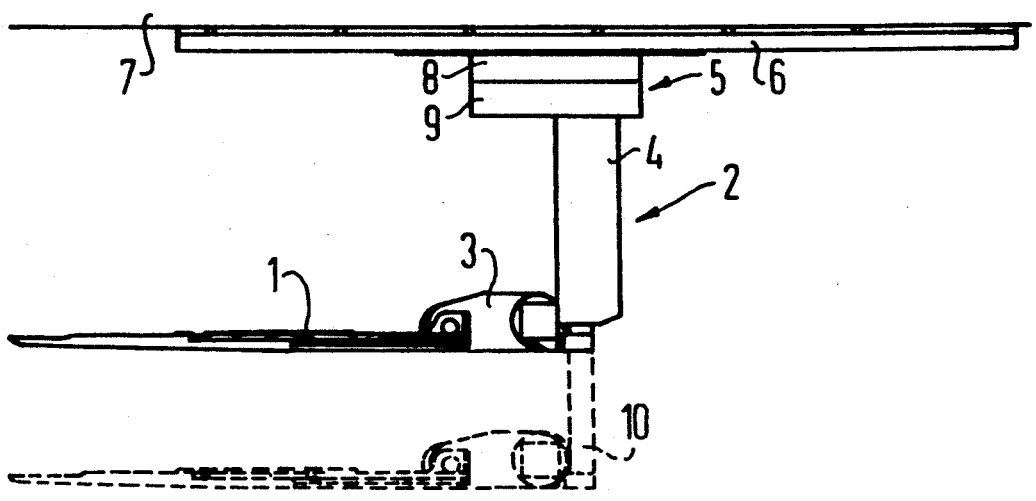
FIG. 1 is a side view of an examination table constructed in accordance with the principles of the present invention.

As shown in FIG. 1, an examination table 1, constructed in accordance with the principles of the present invention, is secured to a stable horizontal surface, in this case the ceiling, via a stand 2 and a tilt mechanism 3 connected at an end of the examination table 1. It will be understood that the table could alternatively be secured to the floor of the examination room. The stand 2 is provided with a column 4 which is secured to a mount 5 which runs in rails 6 fastened to the ceiling 7. The mount 5 is divided into an upper part 8 and a lower part 9, the lower part 9 being displaceable relative to the upper part 8 in directions perpendicular relative to the longitudinal direction of the ceiling rails 6. The column 4 is also provided with an arm 10 which permits the column 4 to be lengthened in downward direction. The examination table 1 can thus be displaced in three orthogonal directions by means of the stand 2.

Figure 2:
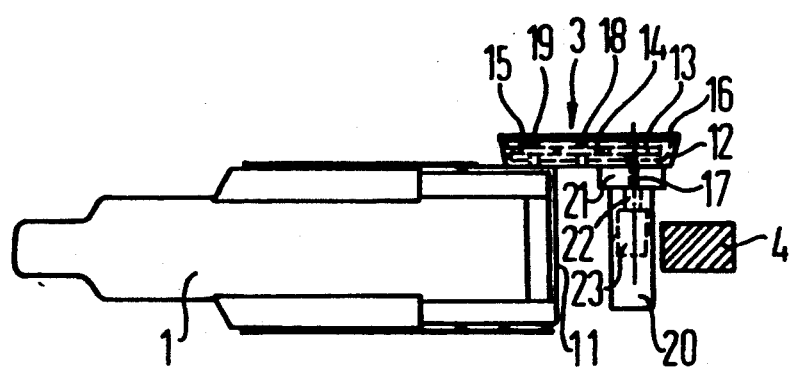
FIG. 2 is a plan view of the examination table of FIG. 1.
Figure 3:
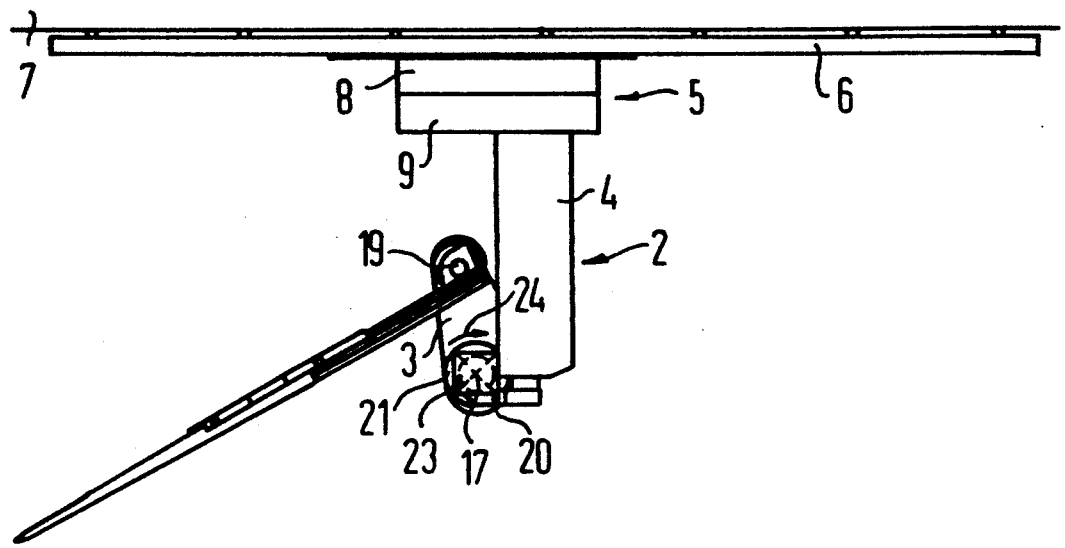
FIGS. 3 and 4 are side views respectively showing the examination table of FIGS. 1 and 2 tilted at different angles.

As can be seen in FIG. 2, the examination table is connected to the tilt mechanism 3 by means of an L-shaped retainer 11. The tilt mechanism 3 includes first and second arms disposed on opposite sides of gears 13, 14 and 15. One of the arms forms a housing 12 for the gears 13, 14 and 15, and the other arm, forms a cover 16 for the housing 12. The gears 13, 14 and 15 mesh in sequence, and have respective axles or shafts 17, 18 and 19 mounted in the housing 12 and in the cover 16. The gear 13 is rigidly attached via its shaft 17 to a boom 20, which is secured to the column 4, and which carries the tilt mechanism 3 and the examination table 1. The gear 15 is rigidly attached to the examination table 1 via its shaft 19. The housing 12 is rigidly connected to a drive mechanism via a drive wheel 21 connected to a drive motor 23 by a shaft 22. The shaft 22 coincides with, or is an extension of, the shaft 17 of the gear 13. By rotating the drive wheel 21 in the direction of the arrow 24 (shown in FIG. 3) using the drive motor 23, the tilt mechanism 3 is also rotated around the shaft 17 in the same direction. As a result, the examination table 1 is rotated in the opposite direction by the tilt mechanism 3, in the manner described in greater detail in connection with FIG. 5, so that the examination table 1 is tilted downwardly around an imaginary axis. During the tilting, the imaginary axis moves in space roughly in the middle of the examination table 1 and transversely relative to the longitudinal axis thereof.

Figure 4:
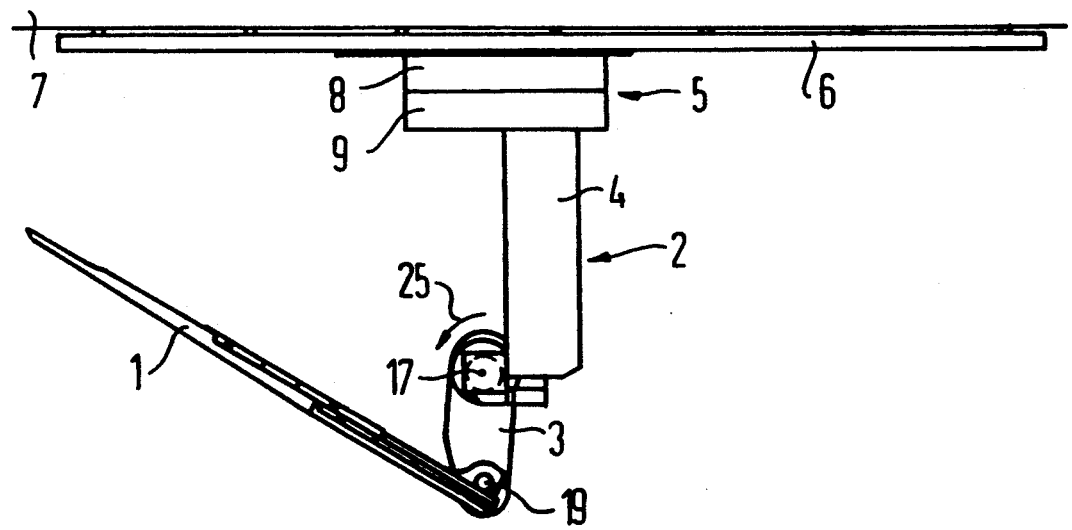

As shown in FIG. 4, the examination table 1 can be also tilted upwardly. This is achieved by rotating the drive wheel 21 (as the aforementioned driven element) by means of the drive motor 23 in the direction of the arrow 25, so that the tilt mechanism 3 is rotated in the same direction around the shaft 17. The examination table 1 is rotated in the opposite direction, so that it is tilted around the aforementioned imaginary axis.

Figure 5:
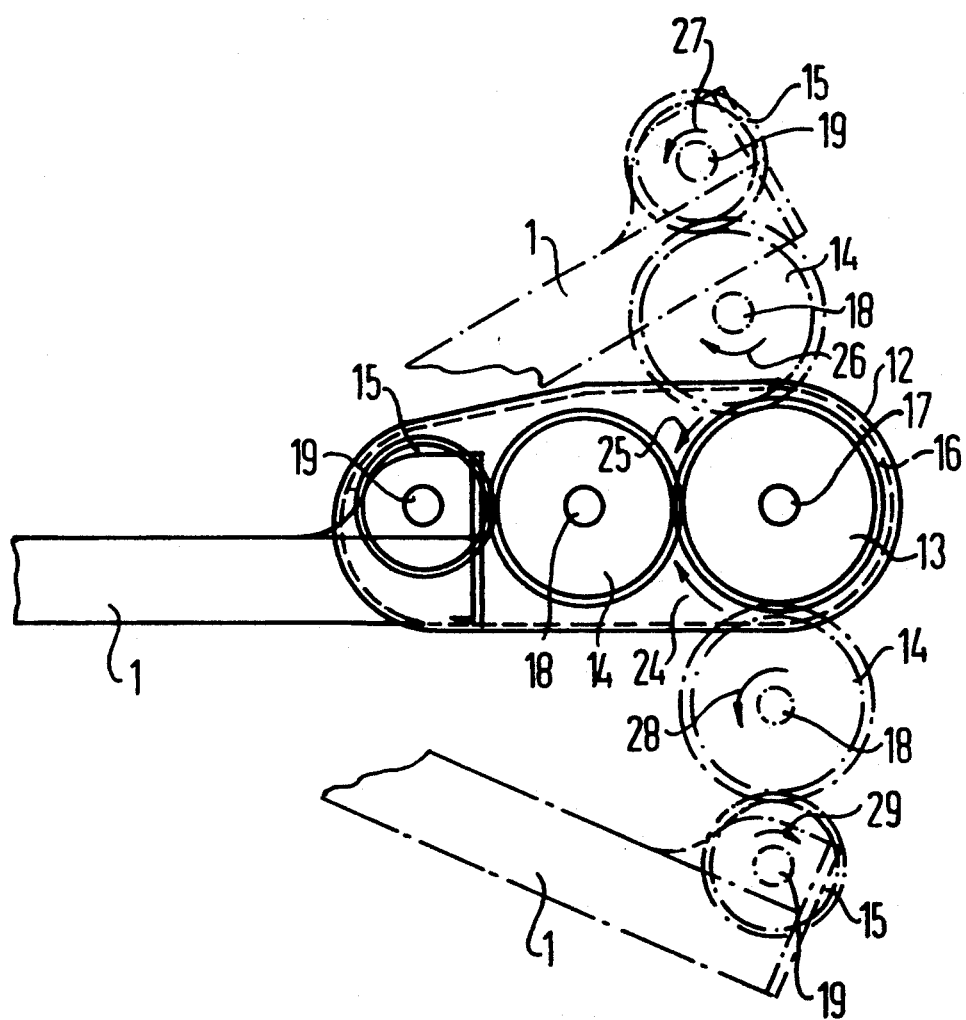
FIG. 5 is an enlarged schematic side view showing details of the tilt mechanism of the examination table constructed in accordance with the principles of the present invention.

The tilt mechanism 3 is schematically shown in FIG. 5. As can be seen, the gears 13, 14 and 15 attached to the housing 12 and to the cover 16 mesh in sequence. As described above, the gear 13 is rigidly attached to the stand 2 by the shaft 17, and the gear 15 is attached to the examination table 1 by the axis 19. The gear 14 is mounted to be rotatable within the housing 12 and the cover 16 via the axle 18. When the drive wheel 21 is driven by the drive motor 23 to rotate around the shaft 17 in the direction of the arrow 24, the housing 12 and the cove 16 are also caused to rotate in the direction of the arrow 24, so that the gear 14 rotates around its axle 18 in the same direction, as shown by the arrow 26 in FIG. 5. The gear 15 is thus caused to rotate in the opposite direction, as shown by the arrow 27, so that the examination table 1 is gradually tilted around the shaft 19 to the position shown in FIG. 3 (and shown in FIG. 5 in dot-dash lines). If the tilt mechanism 3 is rotated around the shaft 17 in the direction of the arrow 25, the gear 14 is rotated around its shaft 18 in the same direction, as shown by the arrow 28. In this manner, the gear 15 is caused to rotate in the opposite direction, as shown by the arrow 29, and the examination table 1 is gradually tilted around the shaft 19 to the position shown in FIG. 4 (and shown in dot-dash lines in FIG. 5).

The tilt angle of the examination table 1 is dependent on the transmission ratio between the gears 13 and 15. The transmission linkage between these gears 13 and 15 can be selected so that other, desired tilt angles can be achieved. In this manner, the imaginary axis around which the examination table is tilted can be displaced.

In a further embodiment of the tilt mechanism, the gear 14 can be replaced by a chain or belt transmission link which connects the gears 13 and 15 to each other. Given such a transmission link between the gears 13 and 15, the housing 12 and the cover 16, which follow the circular motion of the gear 15 around the shaft 17, can be replaced by two parallel plates disposed opposite each other, the gears 13 and 15 being disposed between these two parallel plates and the plates being provided with arcuate slots in which the shaft 19 of the gear 15 can run. The movement of the gear 15 along the arcuate slot in this embodiment is controlled with a drive mechanism.

Although other modifications and changes may be suggested by those skilled in the art, it is the intention of the inventor to embody within the patent warranted hereon all changes and modifications as reasonably and properly come within the scope of his contribution to the art.

I claim as my invention:

1. A patient examination table assembly comprising:
a patient examination table having a longitudinal axis;
a stand supporting said table relative to a stable horizontal surface;
tilting mechanism means, disposed between said table and said stand, for tilting said longitudinal axis of said table up or down relative to said horizontal surface, said tilting mechanism means including a first gear mounted on a first shaft and rigidly attached to said stand, a second gear mounted on a second shaft and rigidly attached to said table, a driveable element to which said second shaft is mounted, and transmission means mechanically linking said first and second gears for rotating said second gear and said table around said first gear when said driveable element is rotated, in a rotational direction opposite to the direction of rotation of said driveable element; and
drive means contained in said stand for rotating said driveable element.

2. A patient examination table assembly as claimed in claim 1 wherein said transmission means comprises an uneven number of gears, said first gear, said uneven number of gears, and said second gear meshing in sequence.

3. A patient examination table assembly as claimed in claim 1 wherein said transmission means is a chain entrained around said first and second gears.

4. A patient examination table assembly as claimed in claim 1 wherein said transmission means is a drive belt entrained around said first and second gears.

5. A patient examination table assembly as claimed in claim 1 further comprising an arm extending parallel to and spaced from said first and second gears, and in which said first and second shafts are received.

6. A patient examination table assembly as claimed in claim 5 wherein said first arm forms said driveable element and is connected to said drive means so that said arm rotates around said first shaft.

7. A patient examination table assembly as claimed in claim 1 further comprising:
a first arm disposed parallel to and spaced from one side of said first and second gears; and
a second arm disposed parallel to said first arm on an opposite side of said first and second gears, said first and second shafts extending between and being received in said first and second arms.

8. A patient examination table assembly as claimed in claim 7 wherein said first arm forms a housing for said first and second gears and for said transmission means and wherein said second arm forms a cover for said housing.

9. A patient examination table assembly as claimed in claim 7 wherein said first arm forms said driveable element is connected to said drive means so that said first arm rotates around said first shaft.

10. A patient examination table assembly as claimed in claim 1 wherein said first shaft is rotatable in said first gear and wherein drive means has a drive shaft connected to said first shaft of said first gear.

11. A patient examination table assembly comprising:
 a patient examination table having a longitudinal axis;
 stand means for supporting said table relative to a stable horizontal surface;
 a first gear mounted on a first shaft and rigidly attached to said stand;
 a second gear mounted on a second shaft and rigidly attached to said table;
 a third gear disposed between and meshing with said first and second gears and rotationally mounted on a third shaft;
 a housing containing said first, second and third gears and in which said first, second and third shafts are mounted; and
 drive means contained in said stand for rotating said housing so that said second gear and said table are rotated around said first gear by intermeshing with said third gear in a rotational direction opposite to the direction of rotation of said housing.

* * * * *